United States Patent
King et al.

(10) Patent No.: US 6,652,871 B1
(45) Date of Patent: Nov. 25, 2003

(54) DELIVERY SYSTEM AND METHOD OF MAKING ARTICLE

(76) Inventors: Joseph A. King, 142 Chevy Chase Dr., Wayzata, MN (US) 55391; Martin Robert Edelson, 7400 Coventry Way, Edina, MN (US) 55439

( * ) Notice: Subject to any disclaimer, the term of this patent is extended or adjusted under 35 U.S.C. 154(b) by 236 days.

(21) Appl. No.: 09/707,114

(22) Filed: Nov. 6, 2000

Related U.S. Application Data

(60) Provisional application No. 60/177,558, filed on Jan. 21, 2000.

(51) Int. Cl.⁷ .................. A01N 25/24; A01N 25/08; A01N 59/16; B01D 63/00
(52) U.S. Cl. .................. 424/407; 210/321.69; 252/181; 424/409; 424/421; 424/618; 427/180; 427/205
(58) Field of Search .............................. 424/407, 421, 424/409, 618; 252/181; 210/321.69

(56) References Cited

U.S. PATENT DOCUMENTS

| | | | |
|---|---|---|---|
| 1,685,204 A | * | 9/1928 | Schreier |
| 2,785,136 A | * | 3/1957 | Colarusso .............. 252/181 X |
| 3,268,444 A | * | 8/1966 | Renn |
| 4,092,245 A | * | 5/1978 | Franks et al. |
| 4,608,247 A | * | 8/1986 | Heinig, Jr. |
| 5,250,118 A | * | 10/1993 | Netwig et al. ...... 210/321.69 X |
| 5,326,573 A | * | 7/1994 | Antfang et al. ......... 424/407 X |
| 5,595,750 A | * | 1/1997 | Jacobson et al. ........... 424/421 |
| 5,849,311 A | * | 12/1998 | Sawan et al. ........... 424/409 X |
| 5,961,843 A | * | 10/1999 | Hayakawa et al. ..... 424/421 X |
| 6,093,422 A | * | 7/2000 | Denkewicz, Jr. et al. ... 424/618 |
| 6,217,892 B1 | * | 4/2001 | King ..................... 424/407 X |
| RE37,890 E | * | 10/2002 | Levy ..................... 424/407 X |

* cited by examiner

Primary Examiner—Richard D. Lovering
(74) Attorney, Agent, or Firm—Jacobson & Johnson

(57) ABSTRACT

A water treatment composition comprised of a metal ion yielding material secured to an adhesive, with the adhesive secured to a structure, so that when the structure is placed in a body of water the concentration of metal ions is maintained at level sufficient to kill bacteria and sufficient to permit release of metal ions over an extended period of time. Also, a method of securing a metal ion yielding material, as well as a method of manufacture of an article, by first adhering the metal ion yielding material to a structure and then forming the structure into an article for placement in a body of water to maintain the desired metal ion concentration therein.

9 Claims, 4 Drawing Sheets

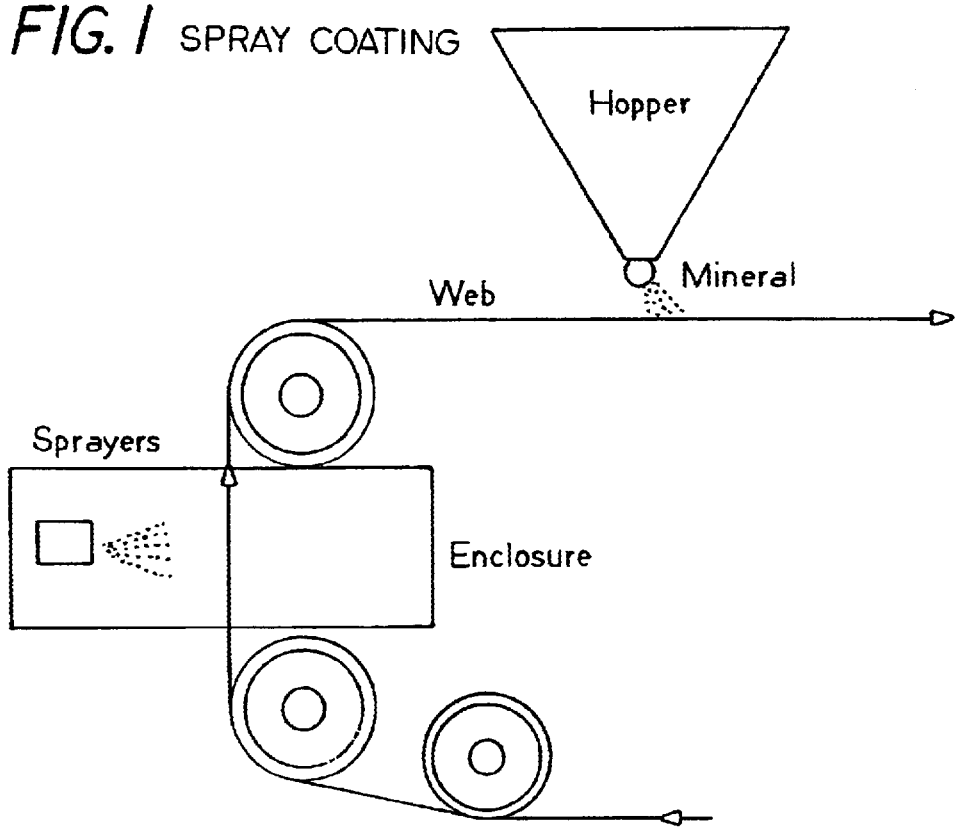
FIG. 1 SPRAY COATING
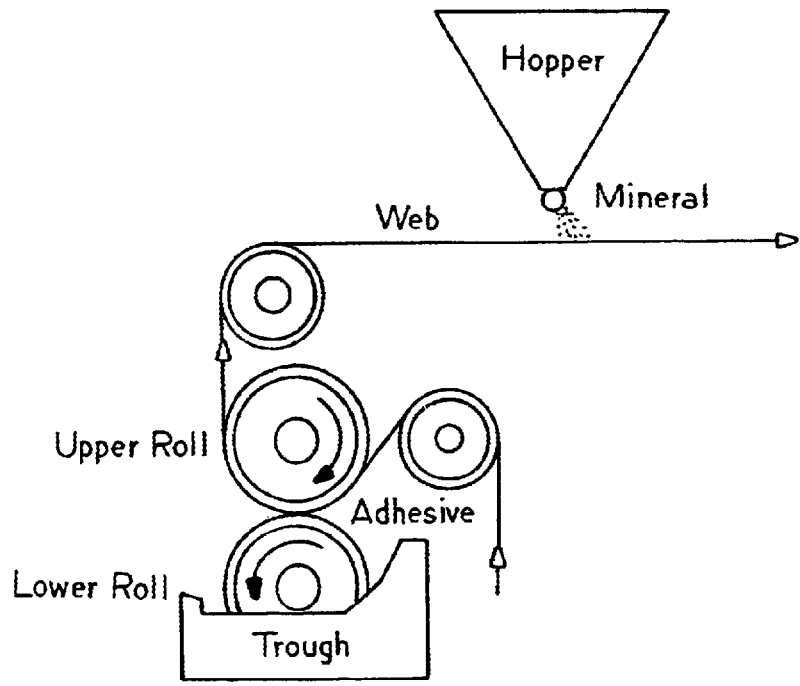
FIG. 2 CALENDAR ROLL COATING

KNIFE-OVER-WEB COATING

IMMERSION COATING: Strips Coated and Inserted in Finished Product

SLURRY COATING: Using Die Coater

SLURRY COATING: Using Calendar Roll Coater

TRANSFER COATING OF SEMI-FINISHED PRODUCT

DIE COATING

DELIVERY SYSTEM AND METHOD OF MAKING ARTICLE

CROSS-REFERENCE TO RELATED APPLICATIONS, IF ANY

This application claims the benefits under 35 U.S.C. §119(e) of provisional application Serial No. 60/177,558, filed Jan. 21, 2000. application Ser. No. 60/177,558, is hereby incorporated by reference.

STATEMENT REGARDING FEDERALLY SPONSORED RESEARCH OR DEVELOPMENT

Not applicable.

REFERENCE TO A MICROFICHE APPENDIX, IF ANY

Not applicable.

FIELD OF THE INVENTION

This invention relates generally to water treatment mechanisms and, more specifically, to the combination of a metal ion yielding material supported by a triple acting adhesive that firstly secures itself to the metal ion yielding material, secondly provides a controlled release of metal ions over a range of water temperatures and thirdly, simultaneously therewith secures the metal ion yielding material to a structure within the water system The invention also relates to a method of manufacture of articles with a metal ion yielding material thereon including methods of securing the metal ion yielding material to a processable material that can be formed into a working or non-working structure that when placed in water to be purified provides a controlled released of metal ions to thereby continually rid the water of bacteria.

BACKGROUND OF THE INVENTION

In water treatment systems it is known that small amounts of metal ions are effective as a bacteria killing material. Suitable metal ions that are use useful in killing bacteria are silver, zinc, copper, and tin. While it is known that such metal ions are effective in killing bacteria in water systems it is necessary to maintain a controlled release of the metal ions in order to provide bacteria killing over an extended period of time. In addition, to provide a controlled release of metal ions, it is necessary to maintain the concentration of metal ions in water at sufficient levels to kill bacteria, yet not sufficiently high so as to cause the metal ions to come out of solution. In addition, as the water system temperature can vary it is desirable to maintain a controlled release of metal ions over a range of water temperatures. In the present invention a metal ion yielding material is maintained in a controlled bacteria killing state by an adhesive that supports the metal ion yielding material in a body of water while simultaneously releasing metal ions to provide for bacteria killing over an extended period of time and in different water temperatures. That is, the adhesive, which remains unreactive to the bacteria killing chemicals, supports the metal ion yielding material in a condition that allows metal ions to migrate therefrom at a sufficiently slow rate so that the metal ion concentration in water remains within acceptable levels.

SUMMARY OF THE INVENTION

Briefly, the present invention comprises a water treatment composition comprised of a metal ion yielding material secured to an adhesive with the adhesive secured to a structure so that when the structure is placed in a body of water the concentration of aqueous metal ions is maintained at levels sufficient to kill bacteria and the secured metal ion yielding material is sufficient to permit release of metal ions over an extended period of time. The invention further comprises methods of securing a metal ion yielding material, as well as a method of manufacture of an article, by first adhering the metal ion yielding material to a structure and then forming the structure into an article that can be placed in a body of water to maintain the proper metal ion concentration therein.

BRIEF DESCRIPTION OF THE DRAWINGS

FIG. 1 shows a method of applying water purification materials to a web using a spray coating method;

FIG. 2 shows a method of applying water purification materials to a web using a calendar roll coating method;

DESCRIPTION OF THE PREFERRED EMBODIMENT

Figure 3:
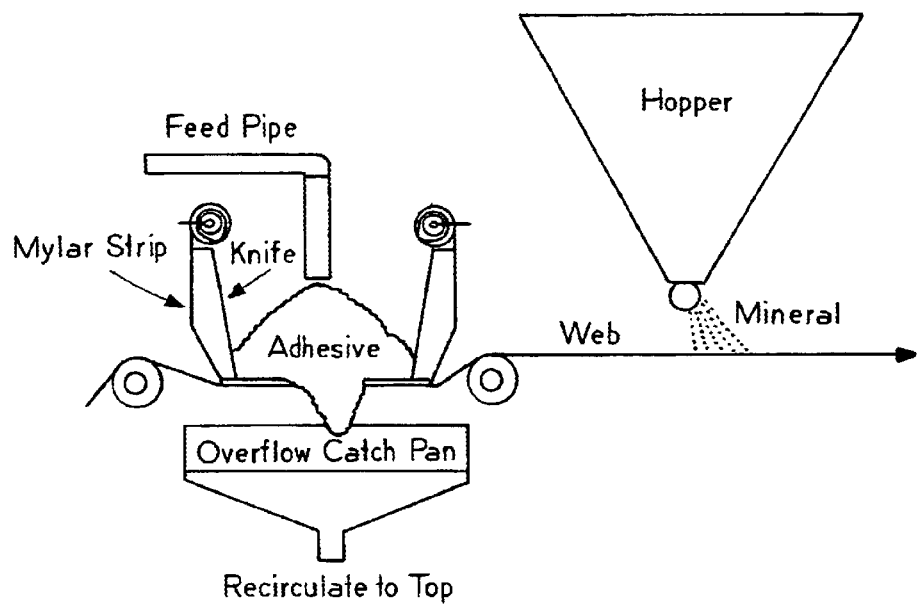
FIG. 3 shows a method of applying water purification materials to a web using a knife-over-web method.

While numerous materials are capable of killing water borne bacteria, not all materials are capable of killing bacteria while remaining non-toxic to humans. In addition, the bacteria killing materials need to be maintained at acceptable levels for an extended period of time in order to provide safe water. It is known that metal ions such as zinc ions, copper ions, silver ions, and tin ions are suitable for killing bacteria However, the use of metal ions requires a delivery mechanism that can both yield the metal ions and maintain the metal ion aqueous concentration within acceptable levels. In the present invention a metal ion yielding material is meant to be understood as one or more compounds that, in the presence of water, yields the metal ions from the compound(s). In the preferred embodiment the metal ion yielding material comprises compounds selected from the group consisting of zinc sulfate, zinc carbonate, zinc chloride, copper chloride, copper carbonate, copper sulfate, silver chloride, stannous chloride and stannic chloride. Each of the above compounds is capable of yielding metal ions. For example zinc carbonate, zinc chloride and zinc sulfate are all capable of yielding zinc ions when placed in water. Similarly, copper chloride, copper carbonate, and copper sulfate all yield copper ions when placed in water. Silver chloride yields silver ions when placed in water and stannous chloride and stannic chloride yield tin ions. Unfortunately, if the metal ion yielding materials are placed directly in water, the concentrations of the metal ions rapidly increase to reach unacceptable levels. For example, if excessive copper ions are present in the water, the copper ions begin to plate out on any fixtures in the pool, thus coating the pool fixtures with an unwanted and unsightly coating of copper. In addition, the surge of metal ions into the water causes a rapid decrease in the ability to provide long term bacteria control. In still other cases metal ion concentrations can rise to levels that could be considered toxic. The present invention provides a water treatment composition wherein the metal ion yielding materials are retained in a condition to controllably release metal ions within acceptable ranges for water treatment. In order to maintain the metal ion yielding materials in a condition to controllably release metal ions into the water, a triple acting adhesive is used. By triple acting adhesive, it is meant that the adhesive can secures itself to dissimilar materials which may be in either solid or particle form. For example, the adhesive should be able to secure itself to a structure and simultaneously secure itself to the metal ion yielding material to hold the metal ion yielding material in position. In addition, the triple acting adhesive needs to maintain its stability over a wide range of water temperatures. The adhesive also needs to limit the amount of metal ions that can be released into the water.

In the preferred embodiment it has been found that four individual triple acting adhesives permit securing itself to the metal ion yielding material and to a separate structure while further maintaining a controlled release of metal ions. The suitable triple acting adhesives are polyurethane, epoxy resin, polyvinyl alcohol, and polyvinyl acetate. A triple acting adhesive selected from the group consisting of polyurethane, epoxy resin, polyvinyl alcohol and polyvinyl acetate provides the controlled release of metal ions from the metal ion yielding materials selected from the group consisting of zinc sulfate, zinc carbonate, zinc chloride, copper chloride, copper carbonate, copper sulfate, silver chloride, stannous chloride and stannic chloride. The preferred triple acting adhesive is polyvinyl acetate. Polyvinyl acetate, which is a non-toxic adhesive, has been found to secure the metal ion yielding material to a structure or to a mineral which is placed in the water and at the same time provides a controlled release of the metal ions. While the mechanism of the controlled release of the metal ions is not fully understood the use of a water insoluble adhesive to secure the ion yielding material to the structure results in a water treatment composition that, when placed in water, maintains the aqueous metal ion concentration at a suitable level for prolonged bacteria killing. Polyvinyl acetate has been found particularly suitable since it is nonsoluble in water and maintains its integrity over a range of water temperatures. For example, a pool may have water at temperatures as low as 70° F. and a hot tub may have water at temperatures as high as 104° F. Polyvinyl acetate is particularly suited for such applications since it has been found that the integrity of polyvinyl acetate is maintained over a wide range of temperatures, while at the same time polyvinyl acetate permits a controlled release of metal ions into the water.

While polyvinyl acetate is the preferred triple acting adhesive, other triple acting adhesives for securing the metal ion yielding material, such as polyurethane, epoxy resin, and polyvinyl acetate, also provide a stable yield of metal ions over an extended range of water temperatures.

With the present invention the metal ion yielding material can be secured to an inactive structure or to an active structure that is placed directly in the water supply. For example, the metal ion yielding material can be affixed to an active structure such as a water filter or to reactive materials that are used to maintain the proper pH of the water supply. A group of suitable materials for maintaining the pH of the water and for supporting the metal ion yielding materials are magnesium carbonate, magnesium silicate, calcium silicate, calcium oxide, silicon dioxide, and calcium carbonate (limestone) or mixtures thereof. Thus, an active structure selected from the group consisting of magnesium carbonate, magnesium silicate, calcium silicate, calcium oxide, silicon dioxide and calcium carbonate or mixtures thereof, provide an active structure that can support the metal ion yielding material thereon.

The following example illustrates how the metal ion yielding material of silver chloride coating was affixed to an active structure of limestone by use of polyvinyl acetate.

EXAMPLE 1

A batch of water treatment composition was prepared using 20 pounds of limestone particles as a structure for carrying the water treatment material and using a spray coating method wherein the triple acting adhesive polyvinyl acetate was mixed with the water treatment material before application to the structure. In order to obtain silver chloride a mixture of 200 grams of silver nitrate was mixed with 74 grams of sodium chloride in a mixture of 403 grams of water and 681 grams of latex polyvinyl acetate. The mixture containing the silver chloride was sprayed on the limestone which was tumbled in a container for ten minutes to distribute the adhesive and the silver chloride over the limestone. The coated limestone was allowed to dry until it was non-tacky to the touch.

The water treatment composition was placed in a test body of water and the total silver ion concentration was measured and ranged from 30 to 40 parts per billion with the silver ion concentration being maintained at less than 100 parts per billion.

A test was conducted to measure the dissolution rate of silver from the silver chloride coated minerals produce in example 1. The test unit included a four liter glass reservoir, a peristaltic pump and a 6" by 1.5" cartridge containing the minerals made in accordance with the method described in example 1. The cartridge containing the minerals was placed in the outlet stream of a reservoir with the outlet of the cartridge returning the water to the top of the reservoir. Four liters of city tap water at 75° F. was added to the reservoir and pumped through the system at a flow rate of 20 milliliters per minute. Water samples were taken from the bottom of the reservoir at the outlet stream of the reservoir at time intervals of 0, 1, 4, 8, 24, 72 and 120 hours. The water samples were analyzed by graphite furnace atomic absorption spectroscopy for determination of the amount of silver present in the form of colloidal silver and silver ions. The results are as follows:

| Time (hours) | Silver (ppb) |
| --- | --- |
| 0 | 1.0 |
| 1 | 4.9 |
| 4 | 18 |
| 8 | 26 |
| 24 | 39 |
| 72 | 39 |
| 120 | 43 |

EXAMPLE 2

A batch water purification composition was made in accordance with Example 1 except an equal amount of polyurethane was used as the binder instead of polyvinyl acetate. The test to determine the amount of silver present was repeated. The results are as follows:

| Time (hours) | Silver (ppb) |
|---|---|
| 0 | 1.0 |
| 1 | 1.0 |
| 4 | 23 |
| 8 | 26 |
| 24 | 33 |
| 72 | 37 |
| 120 | 33 |

In both examples the measured concentration of silver (including colloidal silver and silver ions) was sufficient to kill bacteria yet not sufficiently high so as to introduce problems because of the presence of high levels of metal ions. When the metal ion yielding material yields silver ions, it is desirable to maintain the silver concentration between 10 and 100 ppb (parts per billion). As can be seen from example 1 and 2, within a matter of 4 hours the concentration of silver in the reservoir was within the acceptable range. If the metal ion yielding material yields zinc or tin ions, the acceptable aqueous concentration for metal ions generally range from 100 to 2000 parts per bubble (ppb). If the metal ion yielding material yields copper ions, the acceptable copper ion concentration in the water ranges from 800 to 1000 parts per billion (ppb)

FIG. 1 shows a method of applying water purification materials to a web using a spray coating method. In the spray coating method multiple spray heads can be used to apply the adhesive onto a web moving through a chamber. The purpose of the chamber is to prevent contamination of the work area due to over spraying. After the adhesive is applied to the web, a hopper drops particles of the metal ion yielding material onto the adhesive. The coated web is then allowed to dry and rewound for use in manufacture of an article for placing in a water system for the purposes of purifying the water therein.

FIG. 2 shows a method of applying water purification materials to a web using a calendar roll coating method. In the method using a calendar roll coat two roll coaters are used to roll an adhesive onto a moving web. The rolls are driven and maintained in a squeezing condition on the web in order to control the thickness of the adhesive applied to the web. The lower roller is partially submerged in a trough that contains a liquid adhesive. As the lower roller rotates it transfers the adhesive onto the moving web. The metal ion yielding particles are applied to the moving web from a hopper. The entire web can be coated with the adhesive, or separate bands can be coated with the metal ion yielding material.

FIG. 3 shows a method of applying water purification materials to a web using a knife-over-web method. In this knife-over-web method two steel knives and an adhesive feed assembly are utilized to apply adhesive onto a moving web. Excessive adhesive flows over the web edges and is recirculated. The web covered with adhesive flows under the knife to limit the thickness of the adhesive coating on the web. The metal ion yielding particles are applied to the moving web from a hopper.

Figure 4:
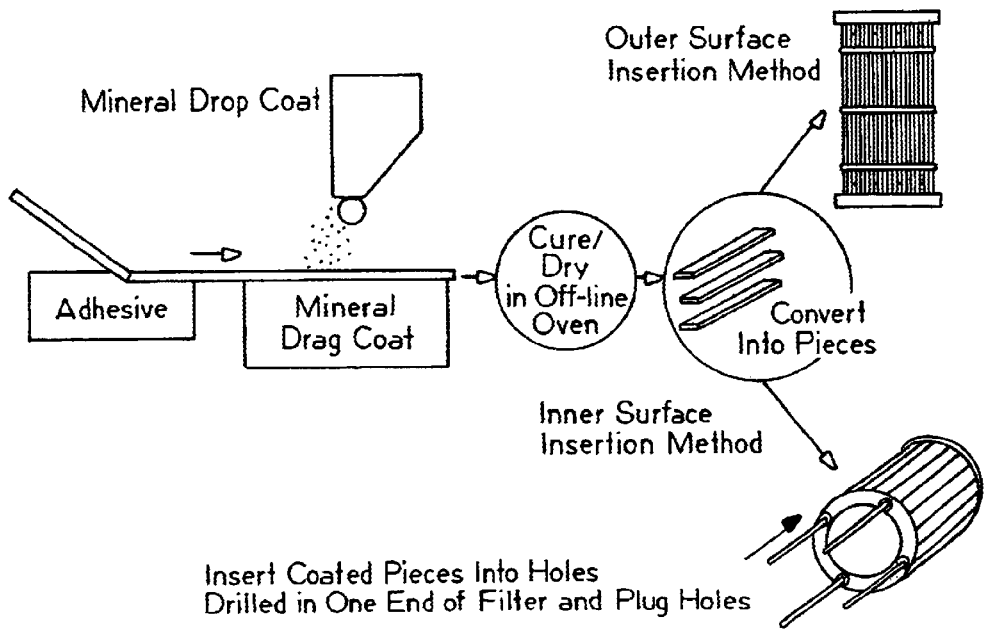
FIG. 4 shows a method of applying water purification materials to strips of material using an immersion coating method.

FIG. 4 shows a method of applying water purification materials to strips of material using an immersion coating method. In the immersion coating method the adhesive is applied to the strips and the metal ion yielding particles are drop coated to the moving article from a hopper. The strips are then adhered to the outside of another structure such as a filter cartridge.

Figure 5:
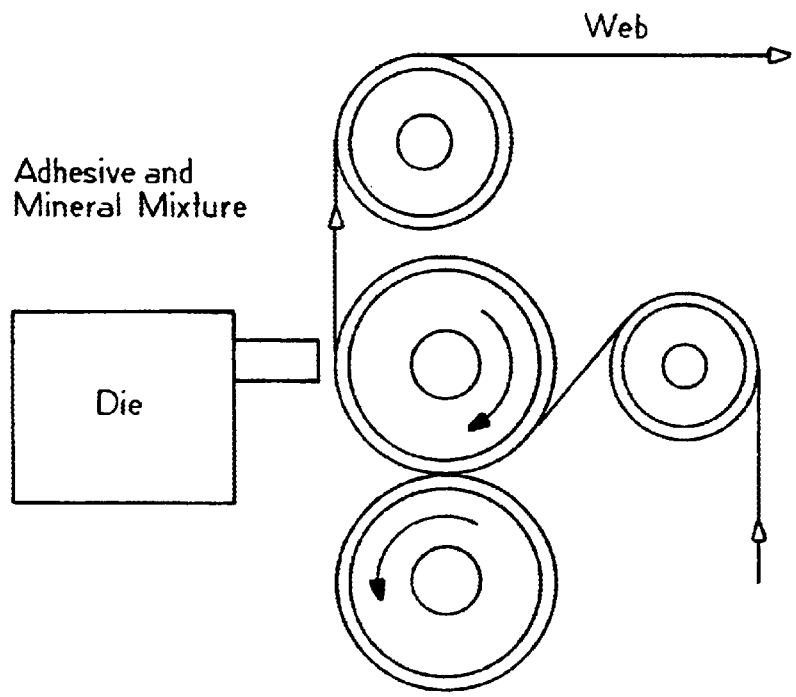
FIG. 5 shows a slurry coating method of applying water purification materials to a web using a die coater.

FIG. 5 shows a slurry coating method of applying water purification materials to a web using a die coater. In the slurry coating-method a pressurized chamber or die is utilized to apply a mixture of adhesive and metal ion yielding metal onto a moving web. In this method the adhesive and metal ion yielding materials are simultaneously applied to the moving web.

Figure 6:
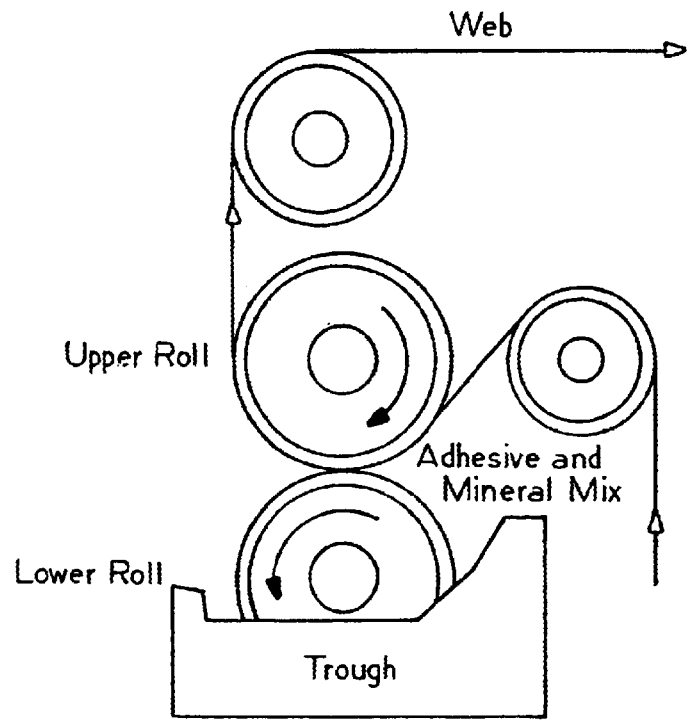
FIG. 6 shows a slurry coating method of applying water purification materials to a web using a calendar roll coater.

FIG. 6 shows another slurry coating method of applying water purification materials to a web using a calendar roll coater. In this slurry coating method the adhesive and the metal ion yielding material are placed in a trough and a roller extends partially into the trough to roll the mixture directly onto a moving web.

Figure 7:
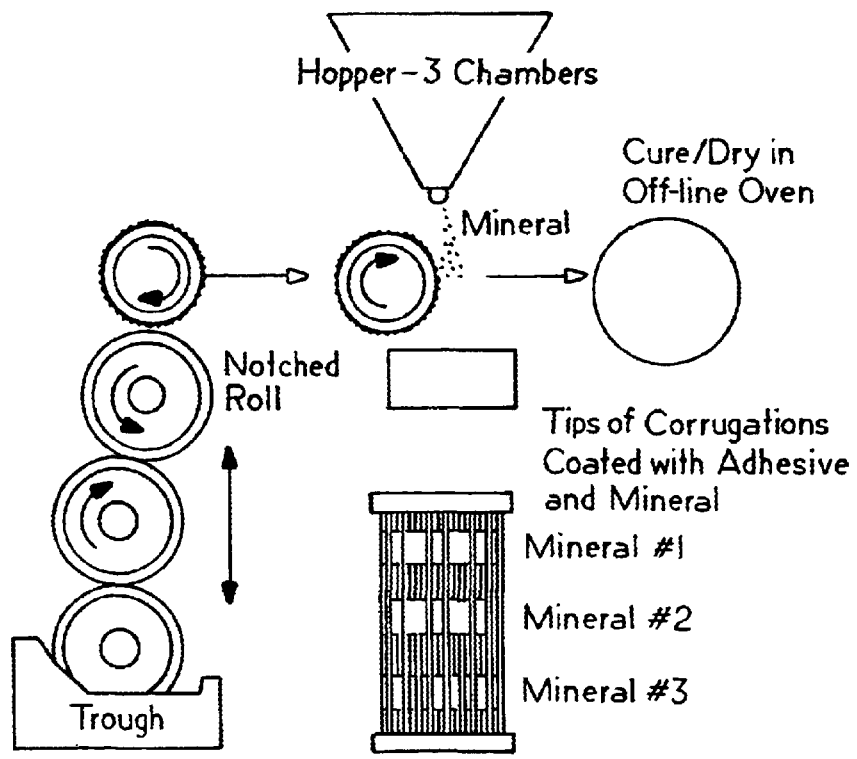
FIG. 7 shows a transfer coating method of applying water purification materials to a semi-finished product.

FIG. 7 shows a transfer coating method of applying water purification materials to a semi-finished product. In this transfer coating method a preassembled article such as filter contains a transfer roll to transfer a layer of adhesive onto the article. A plurality of transfer rollers can be used to limit the amount of adhesive applied to the article. The metal ion yielding material is then dropped onto the adhesive. In the method shown one can apply multiple metal ion yielding materials to the article. That is, one strip could contain a first metal ion yielding material and the other could contain a different metal in yielding material.

Figure 8:
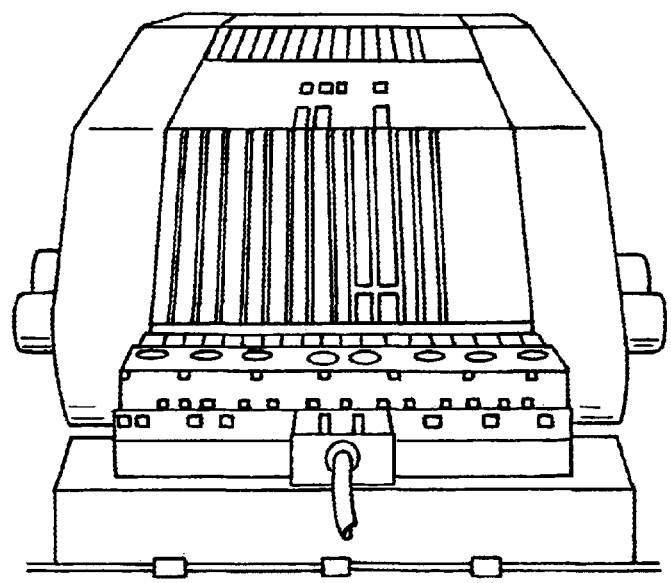
FIG. 8 shows a die coating method of applying water purification materials to a web.

FIG. 8 shows a die coating method of applying-water purification materials to a web. In this die coating method the die coating is applied to a continuous web, and the metal ion yielding material is drop coated on the web.

In the methods of the present invention the water treatment material is applied to the structure by either applying the adhesive to the structure and then applying the metal ion yielding material to the structure or mixing the adhesive with the metal ion yielding material and then simultaneously applying the mixture of adhesive and metal ion yielding material to the structure.

We claim:

1. A water treatment composition for maintaining a metal ion aqueous concentration at a bacteria controlling level comprising:
   a metal ion yielding material selected from the group consisting of zinc sulfate, zinc carbonate, zinc chloride, copper chloride, copper carbonate, silver chloride, stannous chloride and stannic chloride;
   a structure; and
   a triple acting adhesive, said triple acting adhesive secured to at least one of said metal ion yielding materials, said triple acting adhesive further secured to said structure so that when said structure is placed in a body of water the adhesive supports said metal ion yielding material in a condition whereby the adhesive remains secured to the structure and to the metal ion yielding material, with metal ions maintained in water at a concentration sufficient to kill bacteria therein.

2. The water treatment composition of claim 1 wherein the structure is active and comprises particles of material.

3. The water treatment composition of claim 1 wherein the structure is an active structure selected from the group consisting of magnesium carbonate, calcium oxide, and silicon dioxide and mixtures thereof.

4. The water treatment composition of claim 1 wherein the structure is a strip of material with said strip of material secured to a filter cartridge.

5. The water treatment composition of claim 1 wherein the triple acting adhesive is selected from the group consisting of polyurethane, epoxy resin, polyvinyl alcohol, and polyvinyl acetate.

6. The water treatment composition of claim 1 wherein the triple acting adhesive is polyvinyl alcohol.

7. The water treatment composition of claim 1 wherein the structure is an active structure selected from the group consisting of magnesium silicate, calcium silicate, and calcium carbonate (limestone) and mixtures thereof.

8. A water treatment composition for maintaining a metal ion aqueous concentration at a bacteria controlling level comprising:

a metal ion yielding material comprising silver chloride;

a structure; and a triple acting adhesive comprising a polyvinyl acetate, said polyvinyl acetate secured to said silver chloride, said polyvinyl acetate further secured to said structure so that when said structure is placed in a body of water the polyvinyl acetate supports said silver chloride in a condition whereby the polyvinyl acetate remains secured to the structure and to the silver chloride while maintaining an aqueous silver ion concentration between 10 and 100 parts per billion (ppb).

9. A water treatment composition for maintaining a metal ion aqueous concentration at a bacteria controlling level comprising:

a metal ion yielding material comprising silver chloride;

a structure; and a triple acting adhesive comprising a polyvinyl alcohol, said polyvinyl alcohol secured to said silver chloride, said polyvinyl alcohol further secured to said structure so that when said structure is placed in a body of water the polyvinyl alcohol supports said silver chloride in a condition whereby the polyvinyl alcohol remains secured to the structure and to the silver chloride while maintaining an aqueous silver ion concentration in the water sufficient to kill bacteria therein.

\* \* \* \* \*